United States Patent [19]

Isoyama et al.

[11] Patent Number: 5,242,374

[45] Date of Patent: Sep. 7, 1993

[54] LEAK DETECTOR FOR AN INTRA-AORTIC BALLOON PUMP

[75] Inventors: Takashi Isoyama, Tokyo; Sadahiko Mushika, Aichi, both of Japan

[73] Assignee: Aisin Seiki Kabushiki Kaisha, Kariya, Japan

[21] Appl. No.: 858,584

[22] Filed: Mar. 27, 1992

[30] Foreign Application Priority Data

Mar. 29, 1991 [JP] Japan .................................. 3-89023

[51] Int. Cl.⁵ ............................................ A61M 29/00
[52] U.S. Cl. .................................... 600/18; 604/100; 606/192
[58] Field of Search ................................ 600/16–18; 604/67, 96–100; 606/192, 194

[56] References Cited

U.S. PATENT DOCUMENTS

| | | | |
|---|---|---|---|
| 3,698,381 | 10/1972 | Federico et al. | 600/18 X |
| 3,720,199 | 3/1973 | Rishton et al. | 604/100 X |
| 3,769,960 | 11/1973 | Robinson | 600/18 |
| 4,016,871 | 4/1977 | Schiff | 128/64 X |
| 4,733,652 | 3/1988 | Kantrowitz et al. | 128/1 D |
| 4,796,606 | 1/1989 | Mushika | 600/18 |
| 4,832,005 | 5/1989 | Takamiya et al. | 600/18 |
| 5,045,051 | 9/1991 | Milder et al. | 600/16 |

*Primary Examiner*—C. Fred Rosenbaum
*Assistant Examiner*—Corrine Maglione
*Attorney, Agent, or Firm*—Sughrue, Mion, Zinn, Macpeak & Seas

[57] ABSTRACT

The invention is directed to a leak detector for an intra-aorta balloon pump which has a pressure source for pressurizing a primary fluid, a balloon filled with a secondary fluid and inflated thereby, and an isolating device which includes a diaphragm for defining a primary chamber and secondary chamber within the device. The primary chamber is communicated with the pressure source and supplied with the primary fluid, and the secondary chamber is communicated with the balloon and filled with the secondary fluid. The leak detector includes a sensor for detecting a relative position of the diaphragm against at least an inner surface of one of the primary chamber and secondary chamber, and determines a leak of the secondary fluid in response to the relative position of the diaphragm detected by the sensor.

5 Claims, 3 Drawing Sheets

LEAK DETECTOR FOR AN INTRA-AORTIC BALLOON PUMP

BACKGROUND OF THE INVENTION

1. Field of the Invention

The present invention relates to a leak detector for an intra-aortic balloon pump, which uses a fluid of helium gas or the like for inflating a balloon, and more particularly to a detector for detecting a leak of fluid such as helium gas from a balloon inflated by the fluid through an isolating device.

2. Description of the Prior Art

A conventional intra-aortic balloon pump apparatus is disclosed in U.S. Pat. No. 4,733,652, as illustrated in FIG. 3 of the present application, where reference numeral 50 indicates a balloon, 51 a catheter, and 52 a port for introducing helium gas into the balloon 50, respectively. The balloon 50 is adapted to be inflated and deflated by means of helium gas fed through the catheter 51, and is inserted into the patient, usually through the femoral artery either percutaneously or through a partial incision, and advanced until it lies within the thoracic aorta descendens. Then, the balloon 50 is inflated or deflated in synchronous relationship with the pulsation of the heart so as to reduce the load on the left ventricle and increase the amount of coronary blood flow.

In the conventional intra-aortic balloon pump as described above, helium gas is mainly used as the fluid for inflating the balloon, and the balloon is inflated and deflated by introducing and discharging the fluid. Therefore, if the fluid leaks out of the apparatus by some causes, the balloon will not be inflated or deflated sufficiently. Accordingly, a detector for detecting a leak of fluid from the balloon pump has been required for the intra-aortic balloon pump apparatus.

For detecting the fluid leak, a method for visually examining an isolating device of the intra-aortic balloon pump, a method for detecting an extraordinary mass of fluid discharged at the time of feeding the fluid, and the like method have been conventionally used.

However, it is difficult for a person to examine the fluid leak visually. As to the method for detecting the fluid leak by means of the discharged mass of fluid, a certain period of time is needed until the extraordinary mass of fluid is discharged, and it is difficult to establish a stationary monitoring system.

SUMMARY OF THE INVENTION

Accordingly, it is an object of the present invention to provide a leak detector for an intra-aortic balloon pump, which is capable of detecting a fluid leak from the balloon pump automatically.

It is another object of the present invention to provide the leak detector which is capable of evaluating the amount of leaked fluid.

In accomplishing the above and other objects, a leak detector is provided for an intra-aortic balloon pump which has a pressure source for pressurizing a primary fluid, a balloon filled with a secondary fluid and inflated thereby, and an isolating device which includes a diaphragm for defining a primary chamber and secondary chamber within the device. The primary chamber is communicated with the pressure source and supplied with the primary fluid, and the secondary chamber is communicated with the balloon and filled with the secondary fluid. The leak detector comprises means for detecting a relative position of the diaphragm against at least an inner surface of one of the primary chamber and secondary chamber, and means for determining a leak of the secondary fluid in response to the relative position of the diaphragm detected by the detecting means.

The detecting means may comprise a primary sensor for detecting a proximity of the diaphragm to the inner surface of the primary chamber, and a secondary sensor for detecting a proximity of the diaphragm to the inner surface of the secondary chamber.

Preferably, each of the primary and secondary sensors comprises a light emitting element and a photosensor for sensing the light emitted from the light emitting element, both disposed in the isolating device, and the diaphragm preferably includes means for blocking the light emitted from the light emitting element to the photosensor when the diaphragm is positioned proximate to the inner surface of the respective one of the chambers.

BRIEF DESCRIPTION OF THE DRAWINGS

The above stated objects and following description will become readily apparent with reference to the accompanying drawings in which.

DESCRIPTION OF THE PREFERRED EMBODIMENT

Figure 1:
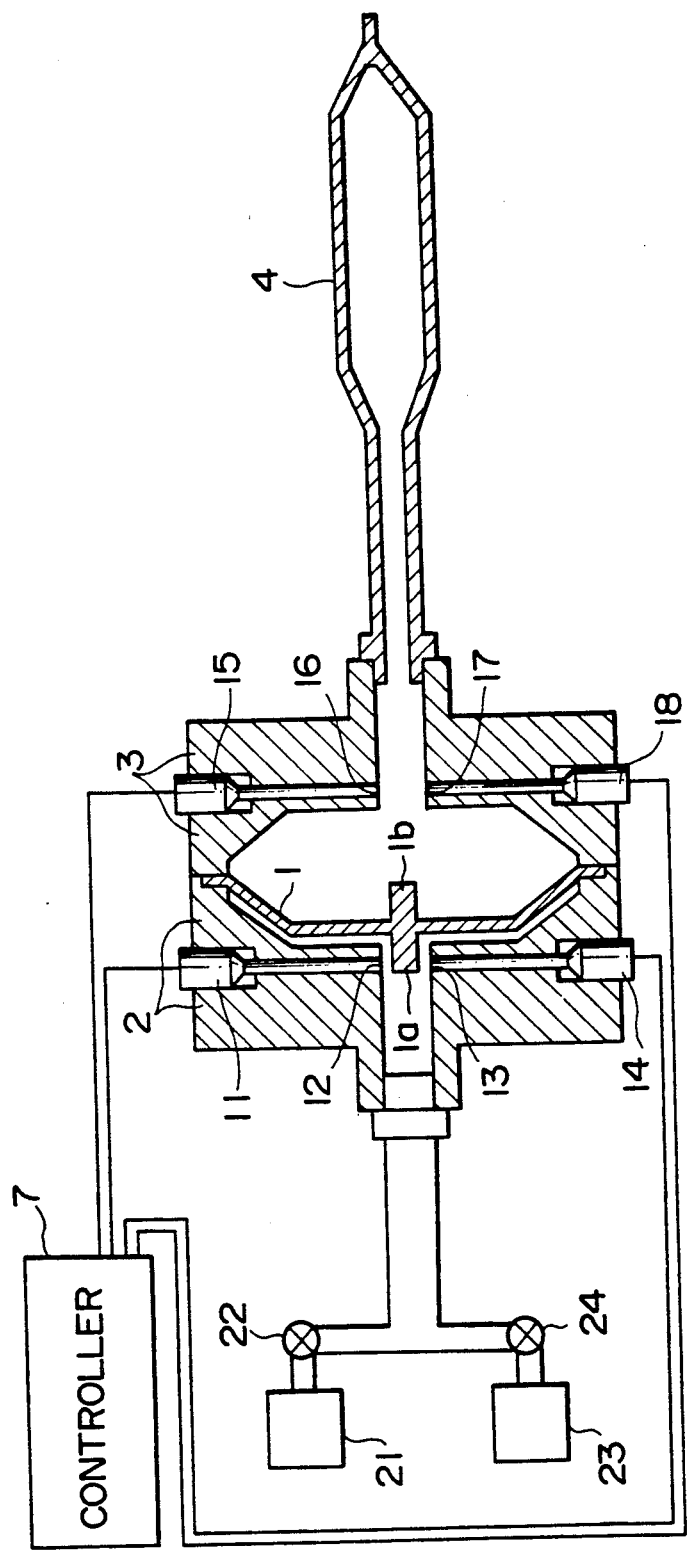
FIG. 1 is a sectional view illustrating an embodiment of a leak detector for an intra-aortic balloon pump according to the present invention.

Referring to FIG. 1, there is illustrated a leak detector for an intra-aortic balloon pump according to an embodiment of the present invention, which has an isolating device. In general, helium gas has been used as a fluid fed into a balloon 4 in consideration of the safety to a patient, whereas air has been used as a fluid to actuate the balloon pump 4 to be inflated and deflated by positive and negative pressure compressors 21, 23. Therefore, the isolating device is provided for separating a fluid at a primary side (normal air), or a primary fluid, from a fluid at a secondary side (helium gas), or a secondary fluid, and also for enabling the pressure transfer between the fluid at both sides. The isolating device includes a primary member 2 for defining a primary chamber into which the primary fluid (normal air) is supplied by the positive pressure compressor 21 and from which the primary fluid is discharged by the negative pressure compressor 23, a secondary member 3 for defining a secondary chamber charged with an amount of secondary fluid (helium gas or the like) adapted to be supplied to the inside of the balloon 4 and a diaphragm 1 held between the primary and secondary members 2 and 3. The diaphragm 1 is made of a soft synthetic rubber, and adapted to separate the primary fluid from the secondary fluid and transfer the pressure of the primary fluid to the secondary fluid.

The primary member 2 is connected to the positive pressure compressor 21 through a tube and a positive pressure timing valve 22 and also connected to the negative pressure compressor 23 through the tube and a negative pressure timing valve 24. In the primary chamber defined between the primary member 2 and the diaphragm 1, there is disposed a sensor for detecting a proximity of the diaphragm 1 to the inner surface of the primary member 2. This sensor employs a transmission-type photoelectric switch which includes a primary light emitting element 11 disposed in the primary member 2, a primary photosensor 14 for receiving the light from the primary light emitting element 11 through a primary light emitting window 12 and a primary light entering window 13 defined in the primary member 2. The diaphragm 1 is formed at one side thereof with a projection 5 which is capable of being positioned between the primary emitting window 12 and the primary entering window 13. Therefore, the sensor is so arranged that when the projection 5 formed on the one side of the diaphragm 1 enters between the primary emitting window 12 and the primary entering window 13, it interrupts or blocks the light emitted from the primary light emitting element 11.

The secondary member 3 is connected to the balloon 4 through a tube, and provided with another sensor for detecting a proximity of the diaphragm 1 to the inner surface of the secondary member 3. This sensor also employs the transmission-type photoelectric switch. Disposed in the secondary member 3, a secondary light emitting element 15 and a secondary photosensor 18 for receiving the light from the secondary light emitting element 15 through a secondary light emitting window 16 and a secondary light entering window 17. The diaphragm 1 is formed at the other side thereof with a projection 6 which is capable of being positioned between the secondary emitting window 16 and the secondary entering window 17. Therefore, the sensor is so arranged that when the projection 6 formed on the other side of the diaphragm 1 enters between the secondary emitting window 16 and the secondary entering window 17, it blocks the light emitted from the secondary light emitting element 15.

Now, the detection of the relative position of the diaphragm 1 against the inner surfaces of the members 2 and 3 made by the sensor will be described in detail. FIG. 1 shows the state in which the diaphragm 1 is in the closest proximity to the inner surface of the primary member 2. The diaphragm 1 may be brought into contact with the inner surface of the primary member 2. In the case where the diaphragm 1 is positioned as shown in FIG. 1, the light emitted from the primary light emitting element 11 and passed through the primary emitting window 12 is blocked by the projection 5 at the one side of the diaphragm 1 and unable to be passed through the primary entering window 13, resulting in no reaction with the primary photosensor 14. That is, the diaphragm 1 is positioned in the closest proximity to the inner surface of the primary member 2. In this case, the light emitted from the secondary emitting element 15 in FIG. 1 is passed through the secondary emitting window 16 and the secondary entering window 17 and is received by the secondary photosensor 18. That is, the diaphragm 1 is positioned remote from the inner surface of the secondary member 3 resulting in a non-contact state therebetween. By detecting the position of the diaphragm 1 against the inner surfaces of the members 2 and 3 in accordance with the above-described manner, it is possible to detect the leakage of the secondary fluid and evaluate the degree of its leaked amount as will be described later. Each of the sensors is adapted to be controlled by a controller 7.

The balloon 4 disposed in the intra-aorta for assisting the heart pulsation is connected to the second member 3, and adapted to be inflated and deflated by means of the positive pressure compressor 21 and the negative pressure compressor 23 as a pressure source, with the diaphragm 1 moved leftward and rightward in FIG. 1. When the positive pressure timing valve 22 is opened and the negative pressure timing valve 24 is closed, the diaphragm 1 is actuated to move in the right direction in FIG. 1, so that the balloon 4 is inflated. On the contrary, when the positive pressure timing valve 22 is closed and the negative pressure timing valve 24 is opened, the diaphragm 1 is actuated to move in the left direction in FIG. 1, so that the balloon 4 is deflated.

Figure 2:
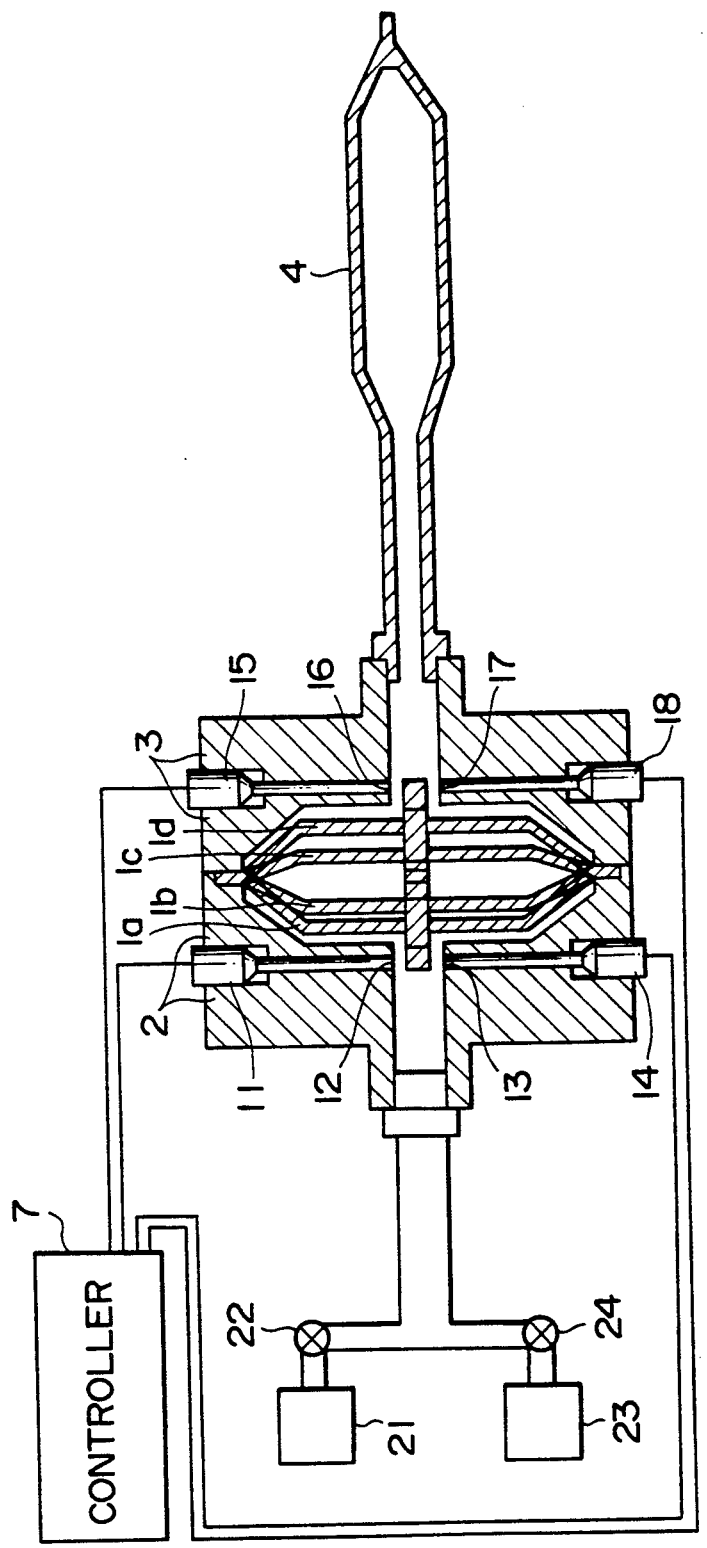
FIG. 2 is a sectional view illustrating the leak detector in operation according to the embodiment of the present invention.
Figure 3:
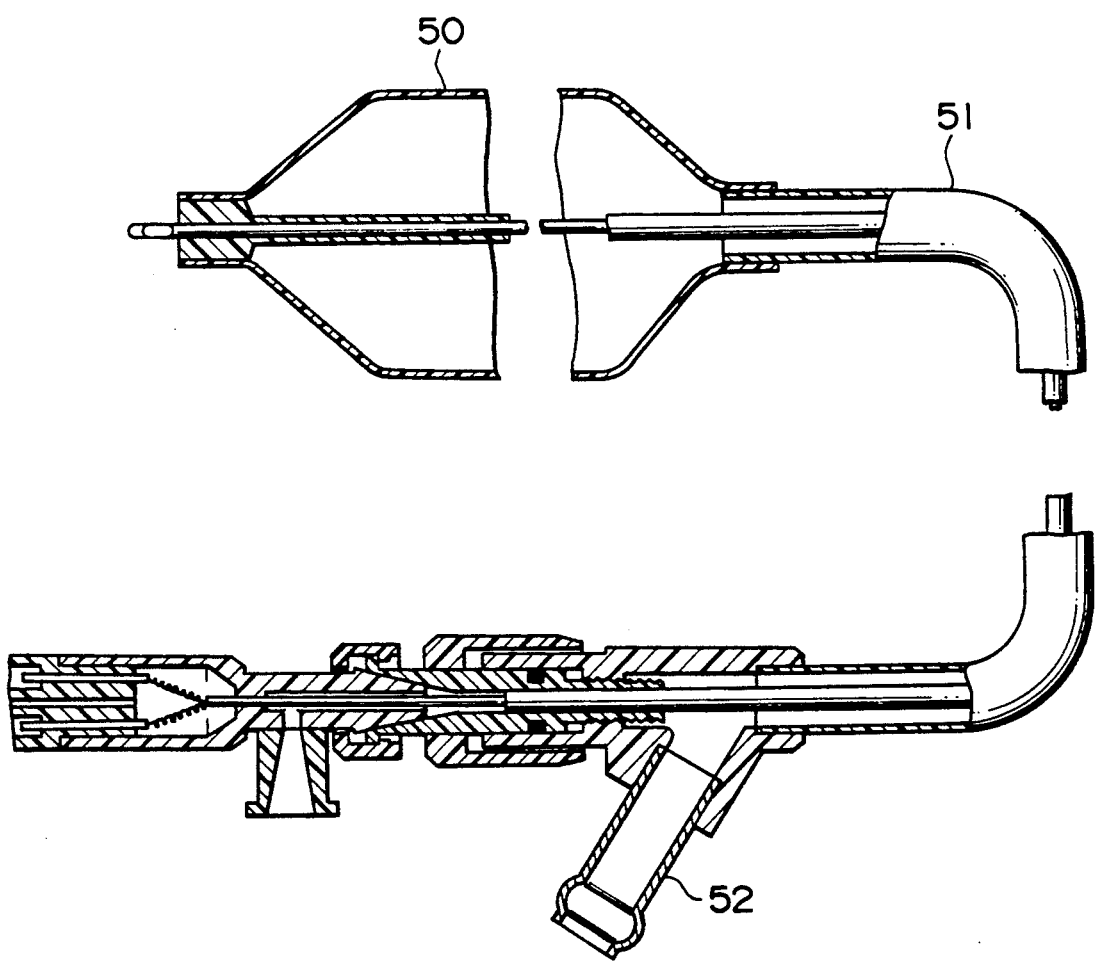
FIG. 3 is a sectional view of an intra-aortic balloon pump according to the prior art.

Referring to FIG. 2, the operation for the leak detector according to the embodiment of the present invention will be described hereinafter. As shown in FIG. 2, the diaphragm 1 may be located at the positions 1a to 1d in accordance with its motion. The position 1a of the diaphragm 1 is the one located at the closest position to the inner surface of the primary member 2. The position 1b of the diaphragm 1 is the one located slightly apart from the inner surface of the primary member 2. The position 1c of the diaphragm is the one slightly apart from the inner surface of the secondary member 3. The position 1d of the diaphragm is the one located at the closest position to the inner surface of the secondary member 3. The diaphragm 1 is designed so as to reciprocate between the positions 1a and 1c in FIG. 2 in a normal condition of the charged amount of the secondary fluid.

In the case where the charged amount of the secondary fluid is sufficient, the primary photosensor 14 comes to a darkened state at the time when the diaphragm 1 is located at the position 1a, upon deflation of balloon 4 and it comes to the lighted state at the time when it is located at other positions In this case, when the charged amount of secondary fluid is sufficient, the secondary photosensor 18 is always in the lighted state (hereinafter, this state will be designated as "never darkened").

In the case where a little amount of the secondary fluid leaks, the diaphragm 1 is unable to reach the position 1a, even in the case where the balloon 4 is deflated due to decrease of the amount of the fluid, so that the diaphragm 1 reciprocates between the positions 1b and 1c. In this case, when there is a small leak, the primary photosensor 14 and the secondary photosensor 18 are both lighted and never darkened. When the secondary fluid leaks further, (large leak) the diaphragm 1 will reciprocate between the positions 1b and 1d. Then, the primary photosensor 14 is never darkened and the secondary photosensor 18 is darkened when the balloon 4 is inflated. In this manner, according to the lighted state and/or darkened state of the primary and secondary photosensors 14, 18, the relative position between the diaphragm 1 and the inner surfaces of the members 2 and 3 can be detected by the sensors, and as a result, it will be possible to detect the leak of the secondary fluid and evaluate the degree of the leaked amount.

The correspondence between the state of each of the photosensors 14, 18 in accordance with the diaphragm 1 located at the positions 1a and 1d and the leak of the secondary fluid is summarized as in Table 1.

TABLE 1

| Relationship between States of Photosensors and Leak of Secondary Fluid | | |
|---|---|---|
| State of Primary Photosensor | State of Secondary Photosensor | Leak of Secondary Fluid |
| Upon deflation of | Never darkened | No leak (Normal) |

TABLE 1-continued

Relationship between States of Photosensors and Leak of Secondary Fluid

| State of Primary Photosensor | State of Secondary Photosensor | Leak of Secondary Fluid |
| --- | --- | --- |
| balloon darkened | | |
| Never darkened | Never darkened | Small leak |
| Never darkened | Upon deflation of balloon darkened | Large leak |

Note:
"darkened": The diaphragm 1 is close to the inner surface of the member 2 or 3.
"Never darkened": The diaphragm 1 is remote from the inner surface of the member 2 or 3.

It should be apparent to one skilled in the art that the above-described embodiments are merely illustrative of but a few of the many possible specific embodiments of the present invention. For example, this invention may be applied to a blood pump of a pulsation-type artificial heart, or the like. Numerous and various other arrangements can be readily devised by those skilled in the art without departing from the spirit and scope of the invention as defined in the following claims.

What is claimed is:

1. A leak detector for an intra-aortic balloon pump having a pressure source for pressurizing a primary fluid, a balloon filled with a secondary fluid and inflated thereby, and an isolating device including a diaphragm for defining a primary chamber and secondary chamber within said isolating device, said primary chamber being connected to said pressure source ad supplied with said primary fluid, and said secondary chamber being connected to said balloon and filled with sad secondary fluid, comprising:

means for detecting a relative position of said diaphragm against at least an inner surface of one of said primary chamber and secondary chamber; and means for determining a leak of said secondary fluid in response to said relative position of said diaphragm detected by said detecting means, wherein said detecting means comprises a primary sensor for detecting a proximity of said diaphragm to the inner surface of said primary chamber, and a secondary sensor for detecting a proximity of said diaphragm to the inner surface of said secondary chamber, and wherein each of said primary and secondary sensors comprises a light emitting element disposed in said isolating device and a photosensor disposed in said isolating device to sense the light emitted from said light emitting element, and wherein said diaphragm includes means for blocking the light emitted from said light emitting element to said photosensor when said diaphragm is positioned proximate to he inner surface of the respective one of said chambers.

2. A leak detector for an intra-aortic balloon pump according to claim 1, wherein said diaphragm is formed at each side thereof with a projection which is capable of being positioned between said light emitting element and said photosensor and which blocks the light therebetween when said diaphragm is positioned proximate to the inner surface of the respective one of said chambers.

3. A leak detector for an intra-aortic balloon pump according to claim 2, wherein said light emitting element and said photosensor are disposed facing each other through a light passage defined in said isolating device, and wherein said projection of said diaphragm is capable of entering into a fluid passage defined in substantially crossed relationship with said light passage.

4. A leak detector for an intra-aortic balloon pump having a pressure source for pressurizing a primary fluid, a balloon filled with a secondary fluid and inflated thereby, a primary member connected to said pressure source, a secondary member connected to said balloon, and a diaphragm disposed between said primary and secondary members for defining a primary chamber with the inner surface of said primary member and defining a secondary chamber with the inner surface of said secondary member, said primary chamber being communicated with said pressure source and supplied with said primary fluid, and said secondary chamber being communicated with said balloon and filled with said secondary fluid, comprising:

a primary light emitting element disposed in a primary light passage defined in said primary member;

a primary photosensor disposed in said primary light passage for receiving the light emitted from said primary light emitting element:

a secondary light emitting element disposed in a secondary light passage defined in said secondary member;

a secondary photosensor disposed in said secondary light passage for receiving the light emitted from said secondary light emitting element; and means for blocking the light emitted from said primary and secondary light emitting elements in response to the movement of said diaphragm.

5. A leak detector for an intra-aortic balloon pump according to claim 4, wherein said blocking means comprises projections formed on both sides of said diaphragm, one of said projections being positioned between said primary light emitting element and primary photosensor when said diaphragm is positioned proximate to the inner surface of said primary chamber, and the other of said projections being positioned between said secondary light emitting element and secondary photosensor when said diaphragm is positioned proximate to the inner surface of said secondary chamber.

* * * * *